US00PP15805P3

(12) United States Plant Patent
Strope

(10) Patent No.: US PP15,805 P3
(45) Date of Patent: Jun. 21, 2005

(54) NEW GUINEA *IMPATIENS* PLANT NAMED 'BALCELICHEY'

(50) Latin Name: *Impatiens hawkeri*
Varietal Denomination: Balcelichey

(75) Inventor: Kerry Strope, Jefferson City, MO (US)

(73) Assignee: Ball Horticultural Company, West Chicago, IL (US)

( * ) Notice: Subject to any disclaimer, the term of this patent is extended or adjusted under 35 U.S.C. 154(b) by 145 days.

(21) Appl. No.: 10/737,399

(22) Filed: Dec. 16, 2003

(65) Prior Publication Data

US 2004/0226066 P1 Nov. 11, 2004

(51) Int. Cl.[7] ..... A01H 5/00

(52) U.S. Cl. ..... Plt./318

(58) Field of Search ..... Plt./318

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct cultivar of New Guinea *Impatiens* plant named 'Balcelichey' characterized by its large bright red-colored flowers, dark green-colored foliage, uniform medium upright, mounded growth habit, and excellent basal branching.

1 Drawing Sheet

Latin name of genus and species of plant claimed: *Impatiens hawkeri.*
Variety denomination: 'Balcelichey'.

BACKGROUND OF THE INVENTION

The present invention relates to a new and distinct New Guinea *Impatiens* plant botanically known as *Impatiens hawkeri* and hereinafter referred to by the cultivar name 'Balcelichey'.

The new cultivar was developed by the inventor in a controlled breeding program during October 1999 at Arroyo Grande, Calif. The objective of the breeding program was to develop New Guinea *Impatiens* cultivars with numerous large flowers, excellent basal branching and upright compact to moderate growth habits.

The female (seed) parent of 'Balcelichey' was the proprietary *Impatiens hawkeri* selection designated 'BFP-2069' (not patented) characterized by its upright growth habit, cherry rose-colored flowers and medium green-colored foliage. The male (pollen) parent of 'Balcelichey' was the proprietary *Impatiens hawkeri* selection designated 'LV36NG760' (not patented) characterized by its upright habit, dark purple-colored flowers, and dark green-colored foliage. 'Balcelichey' was discovered and selected as a single flowering plant within the progeny of the above stated cross-pollination in April of 2000 at Arroyo Grande, Calif. and initially designated '2835-12'.

Asexual reproduction of the new cultivar by terminal stem cuttings in West Chicago, Ill., since 2000, has demonstrated that the new cultivar reproduces true to type with all the characteristics, as herein described, firmly fixed and retained through successive generations of such asexual reproduction.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits large round red-colored flowers,
2. Forms dark green-colored foliage,
3. Exhibits a good basal branching character, and
4. Exhibits a medium, upright mounded growth habit.

Plants of the new cultivar differ from plants of the female parent primarily in foliage color and from plants of the male parent primarily in flower color.

Of the many commercially available New Guinea *Impatiens* cultivars known to the inventor, 'Balcelichey' is most similar to 'Martinique' (U.S. Plant Pat. No. 9,149). However, in side-by-side comparisons conducted in West Chicago, Ill., plants of the new cultivar differed from plants of 'Martinique' in the following characteristics:

1. Plants of the new cultivar are more vigorous than plants of 'Martinique'.
2. Flowers of the plants of the new cultivar are larger than flowers of the plants of 'Martinique'.
3. Plants of the new cultivar have less pubescence on the leaves and stems than plants of 'Martinique'.

BRIEF DESCRIPTION OF THE PHOTOGRAPH

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Balcelichey'. The plants were grown from rooted cuttings for 11 weeks in a greenhouse at West Chicago, Ill.

DETAILED DESCRIPTION

Figure 1:
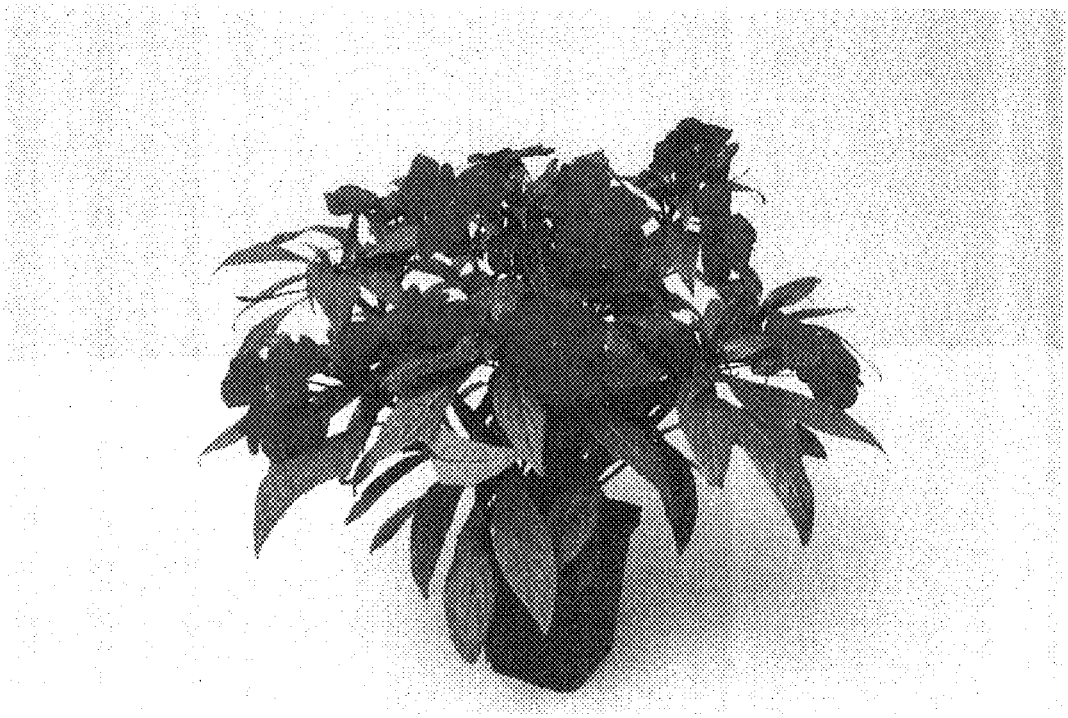
FIG. 1 illustrates a side view of the overall growth and flowering habit of 'Balcelichey'.
Figure 2:
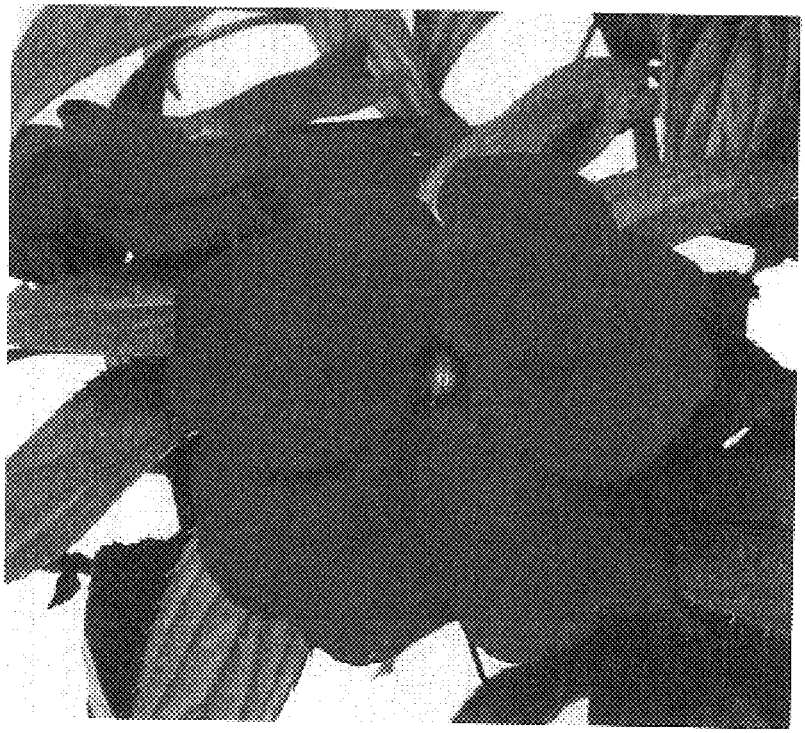
FIG. 2 illustrates a close-up view of a single flower of 'Balcelichey'.

The chart used in the identification of colors described herein is The R.H.S. Colour Chart of The Royal Horticultural Society, London, England, 1995 edition, except where general color terms of ordinary significance are used. The color values were determined on Aug. 15, 2003 between 1:00 and 1:45 p.m. under natural daylight conditions.

The following measurements and comparisons describe plants produced from cuttings taken from stock plants and grown under greenhouse conditions comparable to those used in commercial practice. The plants were grown in 10 cm pots for 11 weeks utilizing a soilless growth medium. Greenhouse temperatures were maintained at approximately 68°–75° F. during the day and approximately 58°–65° F. during the night. Greenhouse light levels were maintained at approximately 4,000–7,000 footcandles during the day.

Classification: *Impatiens hawkeri* cultivar Balcelichey.

Parentage:

*Female (seed) parent.*—Proprietary *Impatiens hawkeri* selection designated BFP-2069 (not patented).

*Male (pollen) parent.*—Proprietary *Impatient hawkeri* selection designated LV36NG760 (not patented).

Propagation:

*Type cutting.*—Terminal stem.

*Time to initiate roots.*—Approximately 7–14 days.

*Time to develop a rooted cutting.*—Approximately 21 days.

*Root description.*—Fine, fibrous.

*Rooting habit.*—Freely branching.

Plant description:

*Habit of growth.*—Moderately vigorous with good basal branching. A mature plant, 11 weeks after the planting of a rooted cutting, commonly measures approximately 25.2 cm from soil level to top of plant plane and approximately 42.2 cm in width (plant spread).

*Plant form.*—Upright and mounded.

*Branches.*—Quantity per plant: Approximately 7. Length: Approximately 14.9 cm. Diameter: Approximately 1 cm. Texture: Glabrous. Color: 144B overlaid with 183A. Internode length: Approximately 5.5 cm.

*Foliage.*—Type: Simple. Arrangement: Alternate. Shape: Elliptic. Apex: Acuminate. Base: Attenuate. Margin: Serrulate, ciliate. Texture of upper and lower surfaces: Glabrous. Venation pattern: Pinnate. Size of mature foliage: Length: Approximately 9.4 cm. Width: Approximately 3 cm. Color of mature foliage: Upper surface: 139A with veins and midvein of 185C. Lower surface: 147B with veins and mid-veins of 185B. Petiole: Length: Approximately 2 cm. Diameter: Approximately 3 mm. Texture of upper and lower surface: Glabrous. Color of upper and lower surface: 185A.

Flower description:

*Flower type.*—Single, not fragrant with self-cleaning petals.

*Flowering habit.*—Freely flowering with flowers positioned above the foliage and facing outward or upward.

*Natural flowering season.*—Year round in greenhouse environment. Flowering is continuous from spring until fall in the garden.

*Flower longevity on plant.*—Approximately 10 days.

*Quantity of flowers and buds per stem.*—Approximately 3 fully open flowers and 5 buds at any one time.

*Mature flower bud (just before opening).*—Shape: Ovate. Length: Approximately 2 cm. Diameter: Approximately 1.3 cm. Color of petals: Closest to 53C.

*Flower shape.*—Round, flat.

*Flower size.*—Diameter: Approximately 7.3 cm. Depth: Approximately 1.3 cm.

*Petals.*—Quantity: Five per flower. Shape: Obovate. Margin: Entire. Apex: Emarginate. Base: Superior petal has truncate base, other four petals have attenuate bases. Texture: Smooth. Appearance: Iridescent. Size: Superior petal length: 2.8 cm. Superior petal width: 4.3 cm. Lateral petal length: 3.8 cm. Lateral petal width: 3.6 cm. Lower petal length: 4.4 cm. Lower petal width: 4.1 cm. Color of upper surface: Lighter and slightly redder than 60A at margin, N66B in center and base. Lower surface: 53D.

*Calyx.*—Quantity of sepals: Three, with base of lower sepal modified into a spur. Sepal shape: Ovate. Sepal apex: Acuminate. Texture of both surfaces: Glabrous. Lateral sepal length: Approximately 1 cm. Lateral sepal width: Approximately 6 mm. Color of both surfaces of lateral sepal: Background of 144C overlaid with 185A. Lower sepal length: Approximately 1.5 cm. Lower sepal width: Approximately 1.1 cm. Color of both surfaces of lower sepal: Background of 62C overlaid with 61C and with veins and margin of 61B.

*Spur.*—Quantity: One per flower. Length: Approximately 5.6 cm. Diameter at flower: 2.6 mm. Diameter at tip: 0.7 mm. Aspect: Curved downward. Color: 53A.

*Peduncles.*—Strength: Strong. Angle to stem: Acute. Length: Approximately 4.8 cm. Diameter: 1.7 mm. Color: 185A.

*Reproductive organs.*—Androecium: Five stamens, anthers are fused together forming one organ that surrounds the pistil. Filaments are free. Generally, the anthers shed pollen prior to the stigma becoming receptive. Filament color: 45B. Anther shape: Oval. Anther length: 3 mm. Anther color: 11D. Pollen amount: Abundant. Pollen color: 10D. Gynoecium: Pistil number: One per flower. Pistil length: 7 mm. Stigma shape: Five pointed star. Stigma length: 0.5 mm. Stigma color: Colorless and translucent. Style length: 0.5 mm. Style color: 154D and translucent. Ovary length: 6 mm. Ovary diameter: 2 mm. Ovary texture: Glabrous. Ovary color: 144A overlaid with N186A.

Seed and fruit development: Neither seed nor fruit production has been observed.

Disease and pest resistance: Resistance to pathogens and pests common to *Impatiens* has not been observed.

What is claimed is:

1. A new and distinct cultivar of New Guinea *Impatiens* plant named 'Balcelichey' substantially, as herein shown and described, which:

1. Exhibits large round red-colored flowers,
2. Forms dark green-colored foliage,
3. Exhibits a good basal branching character, and
4. Exhibits a medium upright, mounded growth habit.

* * * * *